United States Patent
Kilmer et al.

[19]

[11] Patent Number: 6,051,023
[45] Date of Patent: *Apr. 18, 2000

[54] CORNEAL CURVATURE ADJUSTMENT RING AND APPARATUS FOR MAKING A CORNEA

[75] Inventors: Lauren G. Kilmer; Alvin E. Reynolds, both of Tulsa, Okla.

[73] Assignee: KeraVision, Inc., Santa Clara, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/969,216

[22] Filed: Nov. 12, 1997

Related U.S. Application Data

[63] Continuation of application No. 08/515,717, Aug. 16, 1995, abandoned, which is a continuation of application No. 08/282,846, Jul. 28, 1994, Pat. No. 5,505,722, which is a continuation of application No. 08/104,342, Aug. 9, 1993, abandoned, which is a continuation of application No. 07/919,499, Jul. 24, 1992, Pat. No. 5,312,424, which is a continuation of application No. 07/566,667, Aug. 13, 1990, abandoned, which is a division of application No. 07/357,700, May 26, 1989, Pat. No. 4,961,744, which is a continuation of application No. 07/062,790, Jun. 15, 1987, abandoned.

[51] Int. Cl.⁷ ........................................................ A61F 2/14
[52] U.S. Cl. .................................... 623/5; 606/1; 606/166
[58] Field of Search ................................ 606/166, 1, 151; 623/5

[56] References Cited

U.S. PATENT DOCUMENTS

| | | |
|---|---|---|
| Re. 35,974 | 12/1998 | Davenport et al. . |
| 1,147,568 | 7/1915 | Thomson . |
| 1,981,566 | 11/1934 | Nigro . |
| 2,014,995 | 9/1935 | Washer . |
| 2,249,906 | 7/1941 | Longoria . |
| 2,473,968 | 6/1949 | Paton . |
| 2,754,520 | 7/1956 | Crawford . |
| 2,818,866 | 1/1958 | Thomas . |

(List continued on next page.)

FOREIGN PATENT DOCUMENTS

| | | |
|---|---|---|
| 1 366 323 | 11/1964 | France . |
| 1 383 768 | 4/1965 | France . |
| 2 053 398 | 4/1971 | France . |
| 2 354 752 | 1/1978 | France . |
| 2 487 667 | 2/1982 | France . |
| 295 962 | 5/1916 | Germany . |
| 27 19 688 | 5/1978 | Germany . |
| 58-212828 | 12/1983 | Japan . |
| 303 061 | 5/1971 | Russian Federation . |
| 388 746 | 7/1973 | Russian Federation . |
| 1 771 730 | 5/1990 | Russian Federation . |
| 303061 | 5/1971 | U.S.S.R. ................................ 606/166 |
| 637 640 | 5/1950 | United Kingdom . |
| 1 006 102 | 9/1965 | United Kingdom . |
| 2 029 235 | 3/1980 | United Kingdom . |
| 1 601 334 | 10/1981 | United Kingdom . |
| 1601334 | 10/1981 | United Kingdom . |
| 2 095 119 | 9/1982 | United Kingdom . |

OTHER PUBLICATIONS

Blavatskaia, D.E.D. (1966). "The use of intralamellar homoplasty in order to reduce refraction of the eye" *Uberstzt. Aus. Oftalmol. Zh.* 7:530–537 which was apparently translated to *Arch. Soc. Ophthmol.* (1988) 6:311–325 (A complete English translation of original attached).

*Primary Examiner*—Michael H. Thaler
*Attorney, Agent, or Firm*—Morrison & Foerster LLP

[57] ABSTRACT

Surgical apparatus for inserting a plastic, split end, adjusting ring into the stroma of the cornea of the eye wherein the adjusting ring includes, as a part thereof, a dissecting head to part the stroma and provide a pathway for the adjusting ring as the ring is rotated. The ends of the adjusting ring are moved to change the shape of the cornea to a desired shape in accordance with the desired visual correction after which the ends of the adjusting ring are fixably joined to maintain the desired shape.

3 Claims, 14 Drawing Sheets

U.S. PATENT DOCUMENTS

| | | |
|---|---|---|
| 3,064,643 | 11/1962 | Dixon . |
| 3,074,407 | 1/1963 | Moon et al. . |
| 3,656,481 | 4/1972 | Ness . |
| 3,729,968 | 5/1973 | Norris . |
| 4,026,591 | 5/1977 | Cleaveland . |
| 4,053,953 | 10/1977 | Flom et al. . |
| 4,061,146 | 12/1977 | Baehr et al. . |
| 4,205,682 | 6/1980 | Crock et al. . |
| 4,298,004 | 11/1981 | Schachar et al. . |
| 4,319,575 | 3/1982 | Bonte . |
| 4,332,039 | 6/1982 | La Fuente . |
| 4,345,601 | 8/1982 | Fukuda . |
| 4,346,482 | 8/1982 | Tennant et al. . |
| 4,346,713 | 8/1982 | Malmin . |
| 4,357,941 | 11/1982 | Golubdov et al. . |
| 4,382,444 | 5/1983 | Malmin . |
| 4,417,579 | 11/1983 | Soloviev et al. ............ 606/166 |
| 4,423,728 | 1/1984 | Lieberman . |
| 4,429,696 | 2/1984 | Hanna . |
| 4,452,235 | 6/1984 | Reynolds . |
| 4,549,529 | 10/1985 | White . |
| 4,565,198 | 1/1986 | Koeniger . |
| 4,607,617 | 8/1986 | Choyce . |
| 4,614,187 | 9/1986 | Mulhollan et al. . |
| 4,619,259 | 10/1986 | Graybill et al. . |
| 4,646,720 | 3/1987 | Peyman et al. . |
| 4,655,774 | 4/1987 | Choyce . |
| 4,662,370 | 5/1987 | Hoffmann et al. . |
| 4,671,276 | 6/1987 | Reynolds . |
| 4,705,035 | 11/1987 | Givens . |
| 4,766,895 | 8/1988 | Reynolds . |
| 4,961,744 | 10/1990 | Kilmer et al. . |
| 5,312,424 | 5/1994 | Kilmer et al. . |
| 5,318,047 | 6/1994 | Davenport et al. . |
| 5,323,788 | 6/1994 | Silvestrini et al. . |
| 5,505,722 | 4/1996 | Kilmer et al. . |
| 5,645,582 | 7/1997 | Silvestrini . |

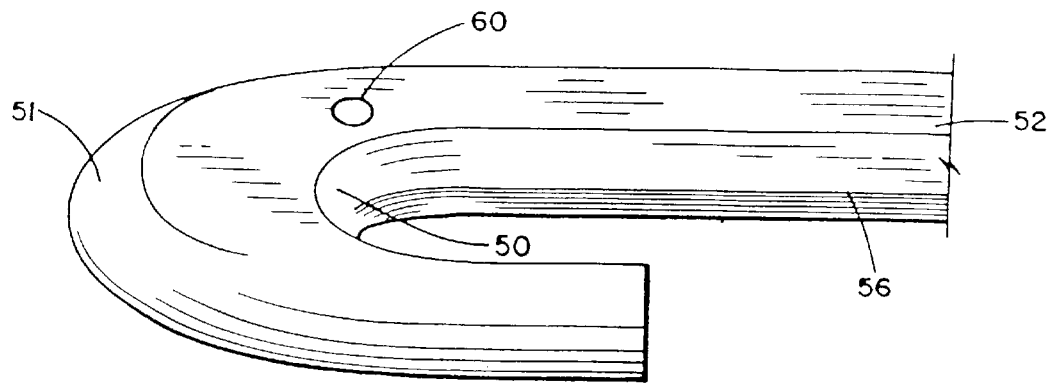
Fig. 8
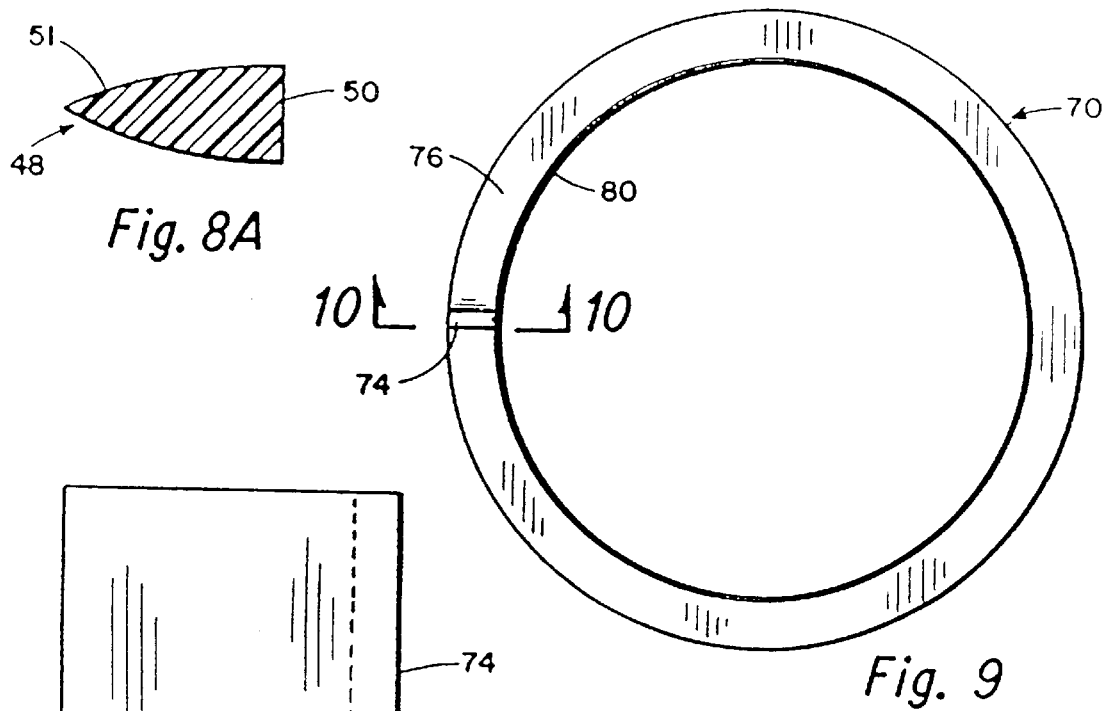
Fig. 8A
Fig. 9
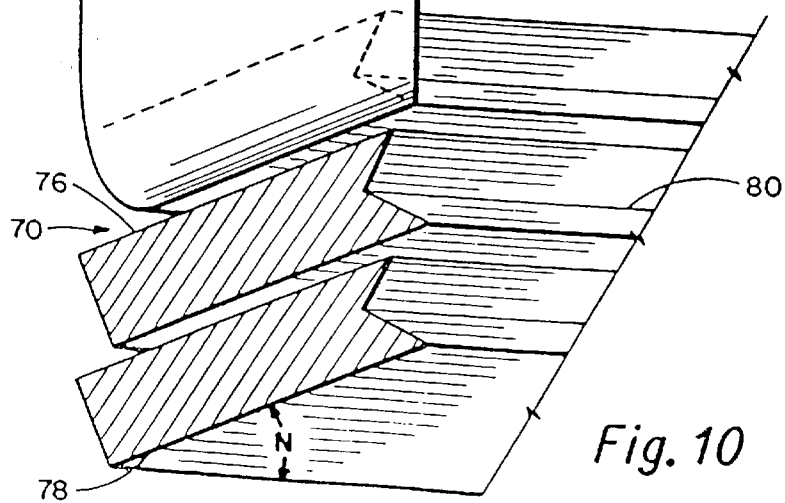
Fig. 10

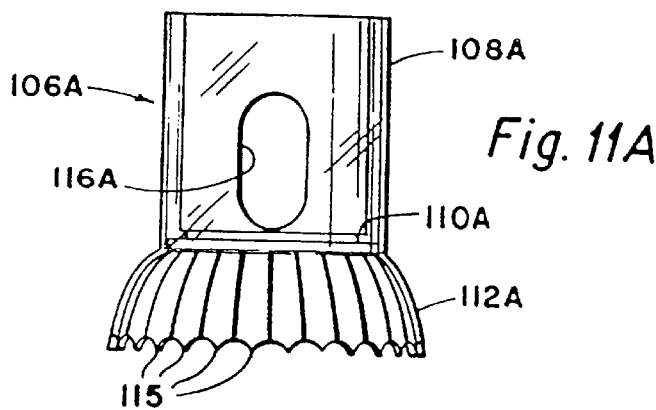
Fig. 11A
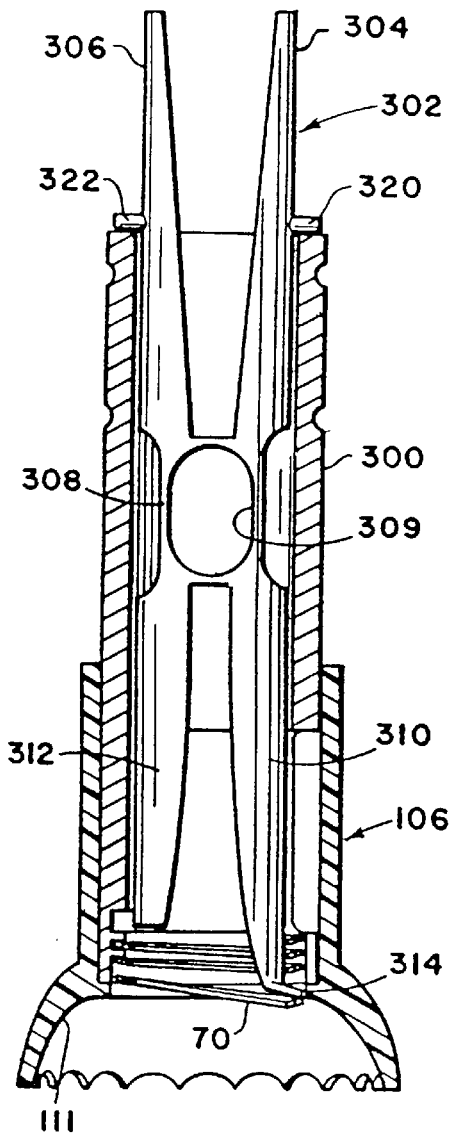
Fig. 12A
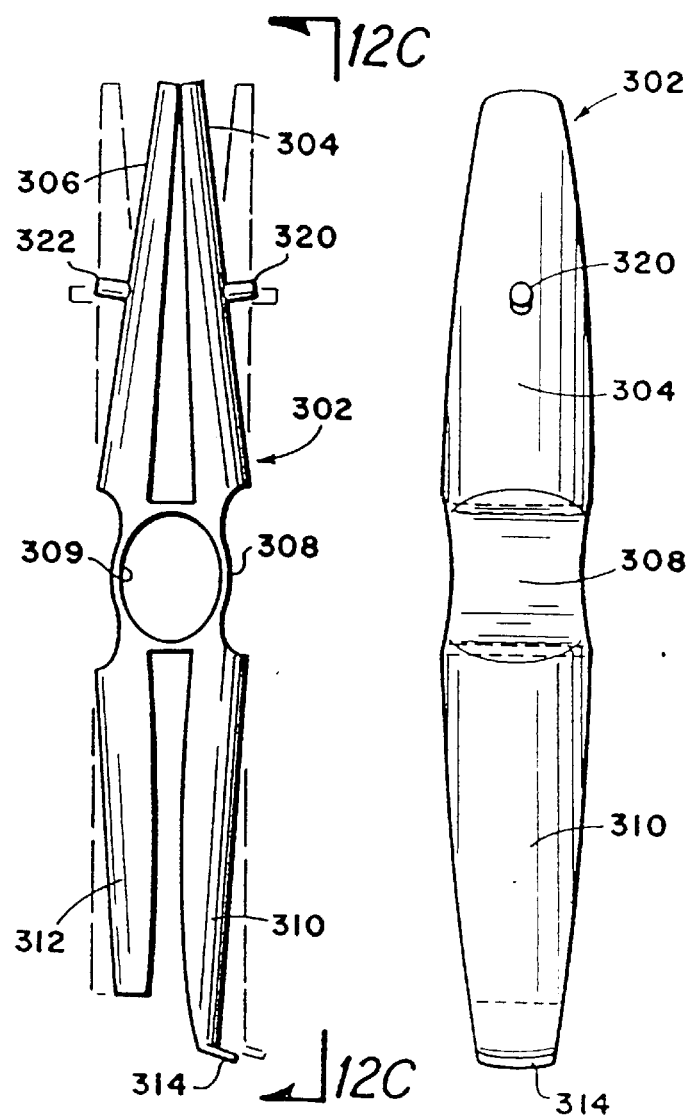
Fig. 12B
Fig. 12C

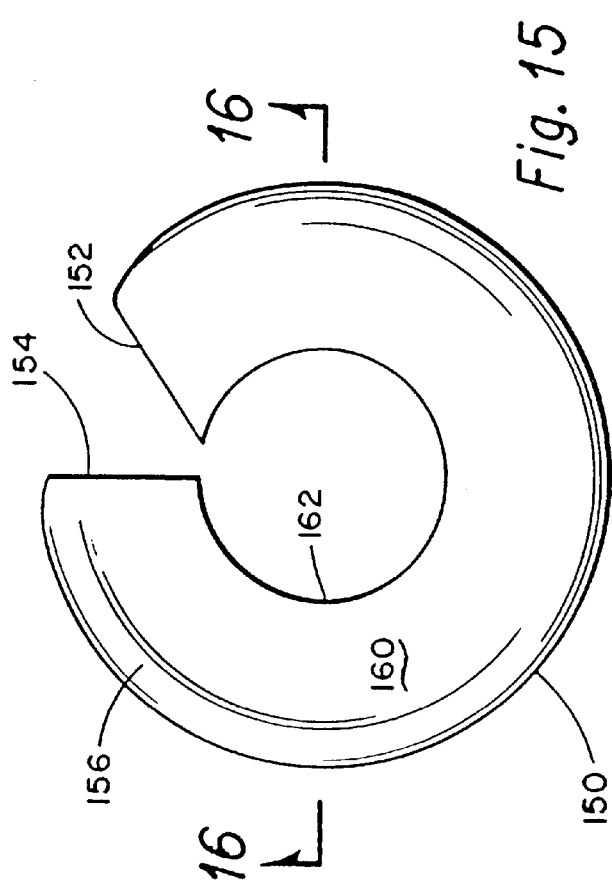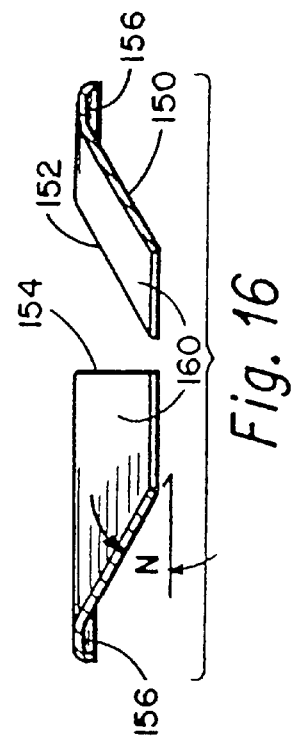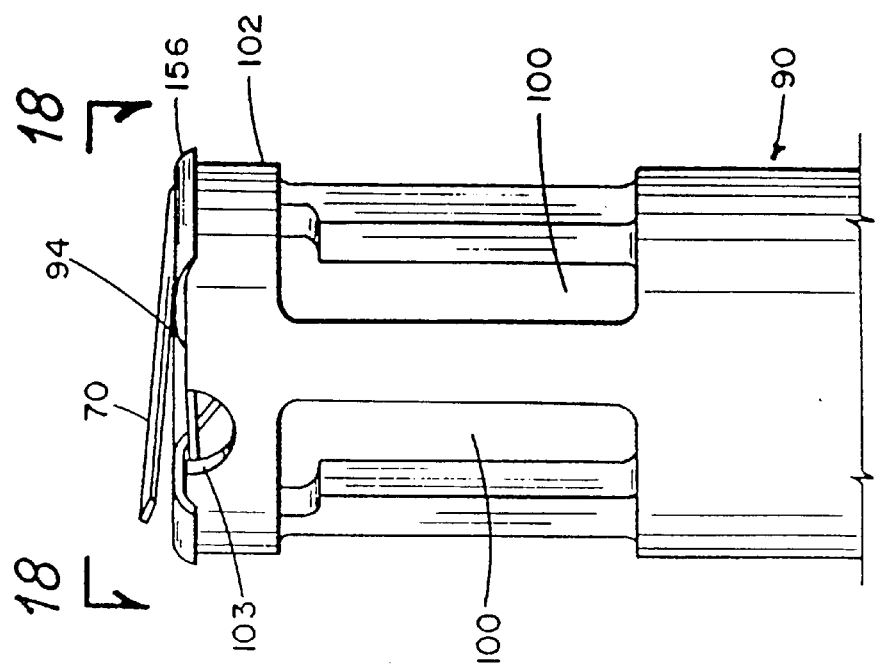

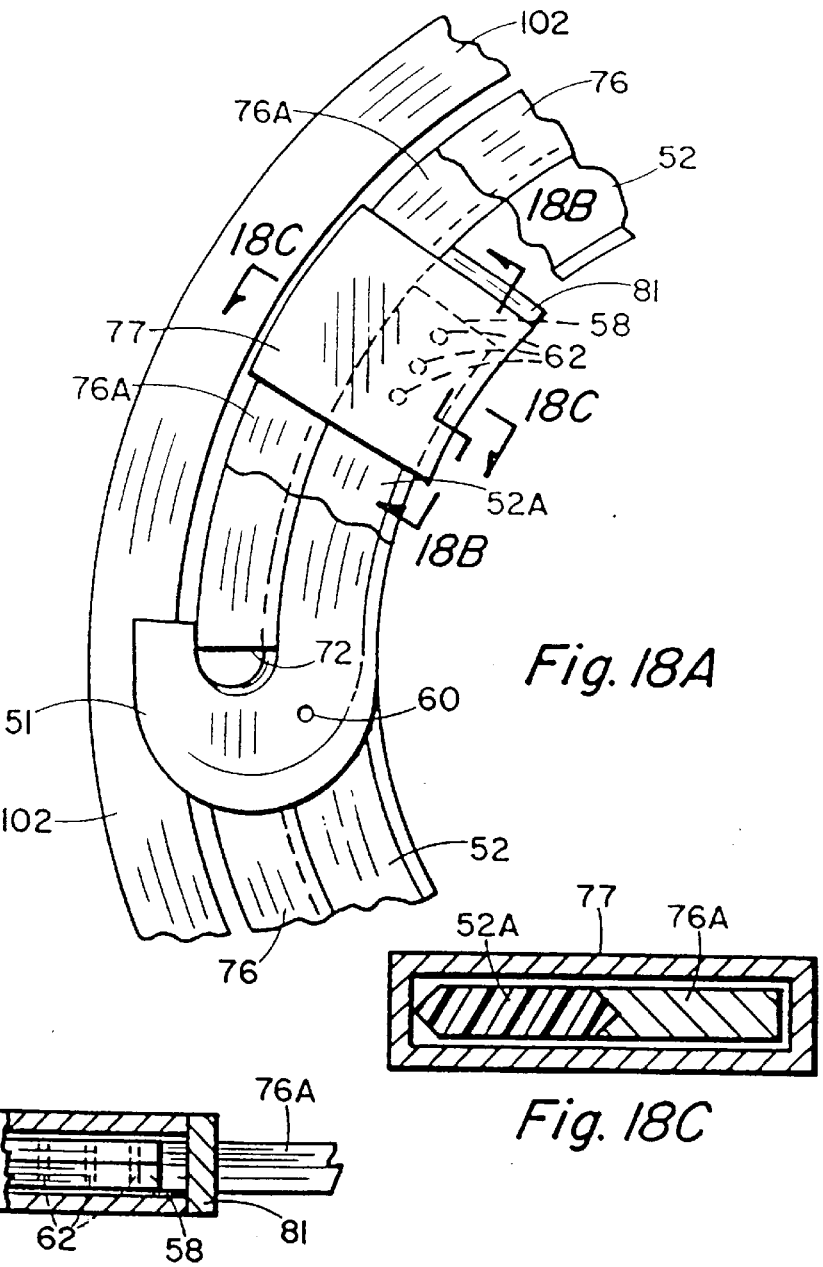
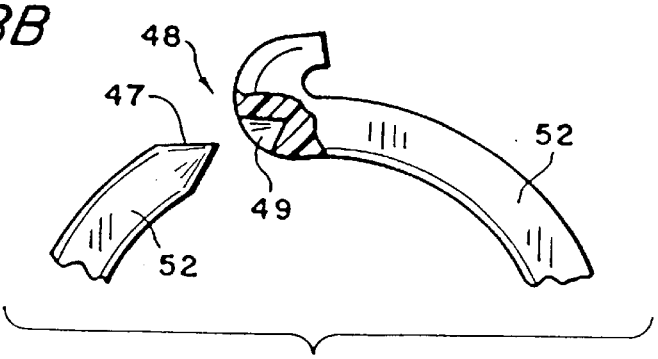
Fig. 18A
Fig. 18C
Fig. 18B
Fig. 18D

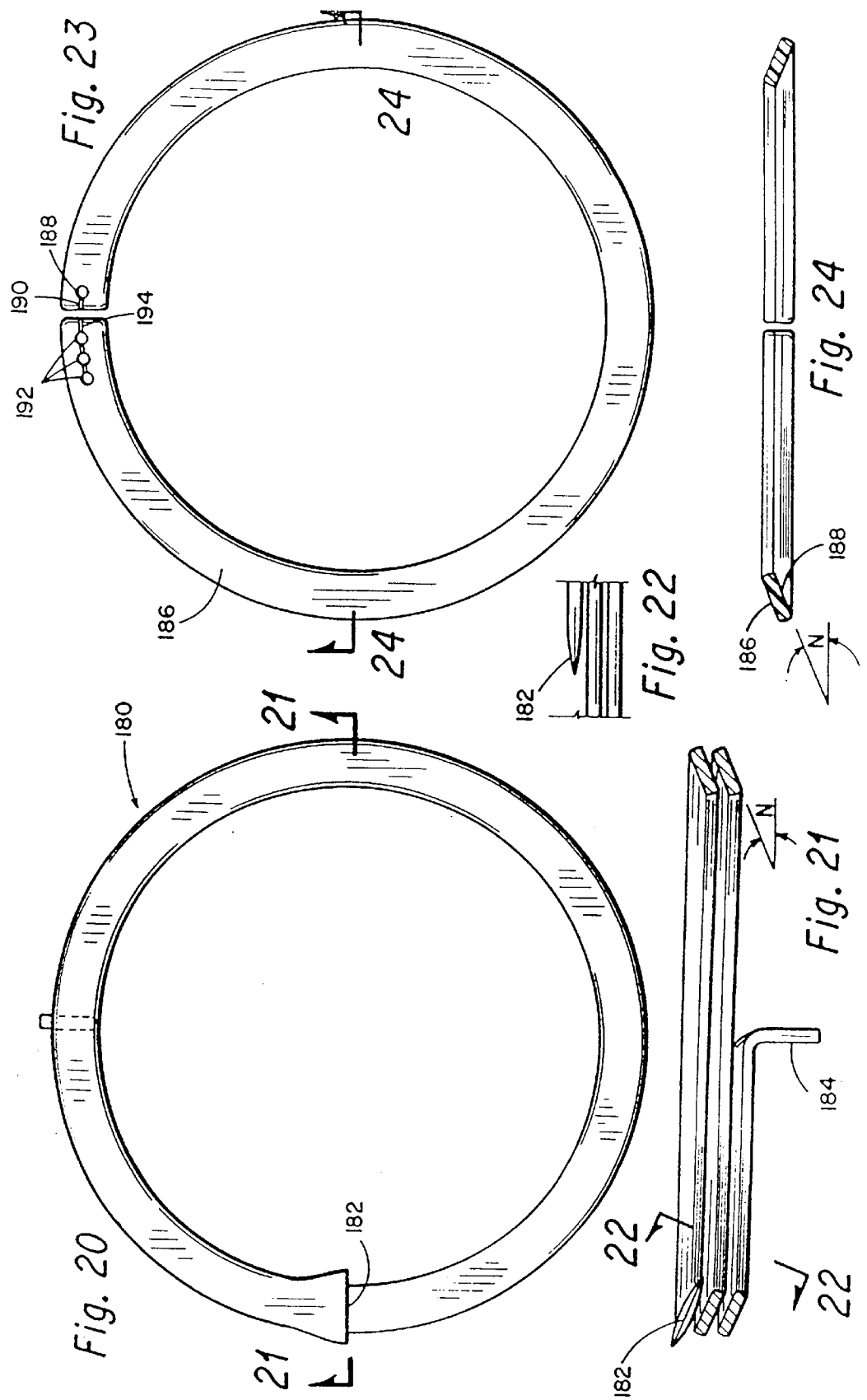

CORNEAL CURVATURE ADJUSTMENT RING AND APPARATUS FOR MAKING A CORNEA

This application is a continuation of application Ser. No. 08/515,717, filed Aug. 16, 1995, now abandoned which is a continuation of application Ser. No. 08/282,846, filed Jul. 28, 1994, now U.S. Pat. No. 5,505,722; which is a continuation of application Ser. No. 08/104,342, filed Aug. 4, 1993, now abandoned; which is continuation of application Ser. No. 07/919,499, filed Jul. 24, 1992, now U.S. Pat. No. 5,312,424; which is a continuation of application Ser. No. 07/566,667, filed Aug. 13, 1990, now abandoned; which is a divisional of application Ser. No. 07/357,700, now U.S. Pat. No. 4,961,744, filed May 26, 1989; which is a continuation of application Ser. No. 07/062,790, filed on Jun. 15, 1987, now abandoned.

BACKGROUND OF THE INVENTION

This invention relates overall to an apparatus for adjusting the shape of the components of the eye and more particularly to making fixed changes in the corneal curvature. Deviations from the normal shape of the corneal surface produce errors of refraction in the visual process. The eye in a state of rest, without accommodation, focuses the image of distant objects exactly on the retina. Such an eye enjoys distinct vision for distant objects without effort. Any variation from this standard constitutes ametropia, a condition in which the eye at rest is unable to focus the image of a distant object on the retina. Hyperopia is an error of refraction in which, with the eye at rest, parallel rays from distant objects are brought to focus behind the retina. Divergent rays from near objects are focused still further back. In one aspect of hypertopia, the corneal surface is flattened which decreases the angle of refraction of rays as they pass through the refractive surfaces of the cornea, causing a convergence or focus of the rays at a point behind the retina. The retina is comprised partially of nerve fibers which are an expansion of the optic nerve. Waves of light falling on the retina are converted into nerve impulses and carried by the optic nerve to the brain to produce the sensation of light. To focus parallel rays on the retina, the hyperopic eye must either accommodate, i.e., increase the convexity of its lens, or a convex lens of sufficient strength to focus rays on the retina must be placed before the eye.

Myopia is that refractive condition in which, with accommodation completely relaxed, parallel rays are brought to focus in front of the retina. One condition which commonly causes myopia is when the corneal curvature is steepened, thus the refraction of rays is greater as they pass through the refractive surfaces of the cornea, and the over refracted rays converge or focus in front of the retina in the vitreous of the eye. When the rays reach the retina they become divergent, forming a circle of diffusion and consequently a blurred image. A concave lens is used to correct the focus of the eye for myopia.

The normal treatment of these classic forms of refractive error of the eye is with the use of eyeglasses or contact lenses, both of which have well-known disadvantages to the user. Recent research has been directed to operative techniques to change the refractive condition of the eye. Such techniques are generally referred to "keratorefractive techniques". Two such techniques are more particularly called keratophakia and keratomileusis. Keratomileusis involves the regrinding of a corneal lamella into a meniscus or hyperopic lens to correct myopia or hyperopia. A corneal optical lathe has been especially developed for this procedure and is also used in the keratophakia procedure, when a homograft ground into a convex lens is placed interlamellarly to correct aphakic hypermetropia. The homograft tissue (corneal lamella) is frozen with carbon dioxide. The homograft is cut as a contact lens would be, i.e., to the optical power required to effect the desired optical correction of the cornea. In keratomileusis, the anterior corneal lamella is shaped by the lathe and in keratophobia, it is the corneal stroma of a donor eye that is shaped by the lathe. These techniques have a broad application in the correction of high hyperopic and myopic errors. These procedures require radial cutting of the cornea about the periphery of the graft which weakens the cornea so that pressure from fluids below the incisions pushes up under the cuts and flattens the curvature of the cornea. This flattening of the cornea results in refractive errors to the eye not compensated for by the graft. Suturing in these operations also causes radial asymmetry of the cornea consequently promotes astigmatic error in this regard. Sutures also cause scarring of the corneal tissue, which scar tissue loses its transparency. Surgical correction of astigmatism is accomplished by asymmetrically altering the corneal curvatures. The effect of a peripherical distorting force may be easily visualized by imagining an inflated balloon with a spherical surface being compressed between the palms of the hands. Because the volume of air in the balloon is constant, the surface area remains constant. The previously spherical anterior surface is distorted meridianally as a result of compressing the diameter between the hands so that the curvature changes without changes the circumference of the surface. The meridian passing over the balloon between the extended fingers steepens, while the uncompressed meridian at right angles thereto flattens as its diameter lengthens in proportion to the shortening of the compressed diameter. This demonstrates the effect that may result from slight variations in the symmetrical patterns or intentional asymmetrical patterns attempted to be accomplished during surgical procedures and attendant suturing. It is thus seen that present procedures in keratorefractive techniques are best limited to situations where other more standard corrective practices are found ineffective. It is readily seen that the limiting factors in such surgical techniques is the gross complexity involved not only with multiple incisions in corneal tissue for affecting the procedures but also complex suturing patterns, resulting in gross restructing of the eye. The eye is thus faced with a difficult job of adjusting to this trauma.

SUMMARY OF THE INVENTION

It is therefore an object of the present invention to provide a new and improved keratorefractive surgical technique involving method and apparatus for changing the shape of the optical zone of the cornea to correct refractive error whereby a minimum disturbance is imposed on the eye system and the simplicity of the technique virtually eliminates the chance of error or further complications resulting from gross disturbances of the eye system.

With this and other objects in view of the present invention contemplates a method and apparatus involving inserting one end of a split end adjusting ring in the cornea of the eye and moving the ring in a circular path until its ends meet, whereby the ends are adjusted relative to one another until the shape of the eye has assumed a desired curvature whereupon the ends are fixedly attached to maintain the desired curvature of the cornea.

Another aspect of the invention involves an adjusting ring which when inserted in the cornea is arranged to have its major cross sectional axis aligned or substantially parallel with a corneal arc extending through the anterior pole of the cornea.

An important aspect of the invention is directed to the use of an adjustment ring holder which is capable of being positioned about the cornea so as to orient a dissecting and/or adjustment ring to have its major cross sectional axis to be aligned or substantially parallel to the corneal arc formed by the anterior pole of the cornea as the holder is rotated.

A yet further aspect and object of the invention is to provide a combination dissecting/adjustment ring in which the forward end thereof dissects or parts the stroma portion of the cornea as the adjustment ring is inserted. Once inserted, the ring is adjusted to create within the cornea, the desired optical correction for that patient.

In still a further object of the invention, one embodiment provides for a drive ring is interconnected with the dissecting/adjusting ring at one end while the other end is interconnected with a ring holder. Rotation of the ring holder and attached drive ring and the interconnected dissecting/adjusting ring is rotated until the dissecting/adjusting ring has been fully inserted into the cornea after which reverse rotation will leave the adjusting ring in place while removing the drive ring.

A further aspect and object of the invention is directed to a dissecting/adjustment ring and an edge coiled drive ring which are preformed at a bevel or slope substantially corresponding to the slope of the corneal are formed by the anterior pole of the cornea.

A further object of the invention is to provide a ring holder that includes means for orienting a dissecting/adjustment ring and/or a drive ring at a slope substantially corresponding to the slope of the corneal arc of the anterior pole of the cornea.

A further aspect of the invention is directed to a holder that has means at the bottom thereof for properly positioning and maintaining the holder at a desired axis to the cornea. At the bottom of the holder are means to retain an adjustment ring and/or an associated drive ring which are pre-disposed at a slope substantially corresponding to the slope of the corneal arc formed by the anterior of the cornea. The holder is positioned within a cylindrical top portion of a transparent guide cup so as to be rotatable therein. The cylindrical top portion is connected to a bottom semi-spherical skirt of larger diameter than said top portion. An interior shoulder is formed at the junction of the top portion and the skirt to rotatably support the holder so as to be oriented relative to the cornea for the insertion of the adjusting ring.

BRIEF DESCRIPTION OF THE DRAWINGS

FIG. 8 is a perspective view of the dissecting head of the dissecting/adjusting ring taking along the line 8—8 of FIG. 5.

FIG. 8A is a sectional view taken along the line 8A—8A of FIG. 5.

FIG. 9 is a top elevational view of a coiled drive ring used to drive the dissecting/adjusting ring of FIG. 5.

FIG. 10 is a sectional view taken along the line 10—10 of FIG. 9.

FIG. 11A is an alternate embodiment of a guide cup.

FIG. 12A is a sectional view of the aforedescribed ring holder of FIG. 11 depicting an alternative embodiment of a ring orientation tool.

FIGS. 12B and 12C show respective front and side elevational views of the ring orientation tool of FIG. 12A.

FIG. 15 is a bottom elevational view of a ring support cup used in conjunction with the ring holder of this invention.

FIG. 16 is a sectional view taken along the line 16—16 of FIG. 15.

FIG. 17 is a partial bottom elevational view of the ring holder of this invention with the ring support and assembly cup and drive ring assembled therewith.

FIG. 18A is a partial view bottom plan of an alternative embodiment.

FIG. 18B is a view, partly sectional, taken along the line 18B—18B of FIG. 18A.

FIG. 18C is a sectional view taken along the line 18C—18C of FIG. 18A.

FIG. 18D is a partial sectional view showing an alternate means for inner connecting the ends of the adjustment ring.

FIG. 20 is a top elevational view of dissecting ring capable of use with the ring holder of this invention.

FIG. 21 is a sectional view taken along the line 21—21 of FIG. 20.

FIG. 22 is a partial sectional view taken along the line 22—22 of FIG. 21.

FIG. 23 is a top elevational view of an adjustment ring for use in conjunction with the dissecting ring of FIG. 20.

FIG. 24 is a sectional view taken along the line 24—24 of FIG. 23.

DESCRIPTION OF THE PREFERRED EMBODIMENT

Before explaining the present invention in detail, it is to be understood that the invention is not limited to its application to the details of construction and arrangement of parts illustrated in the accompanying drawings, since the invention is capable of other embodiments and of being practiced or carried out in various ways commensurate with the claims herein. Also it is to be understood that the phraseology or terminology employed herein is for the purpose of description and not of limitation.

Figure 1:
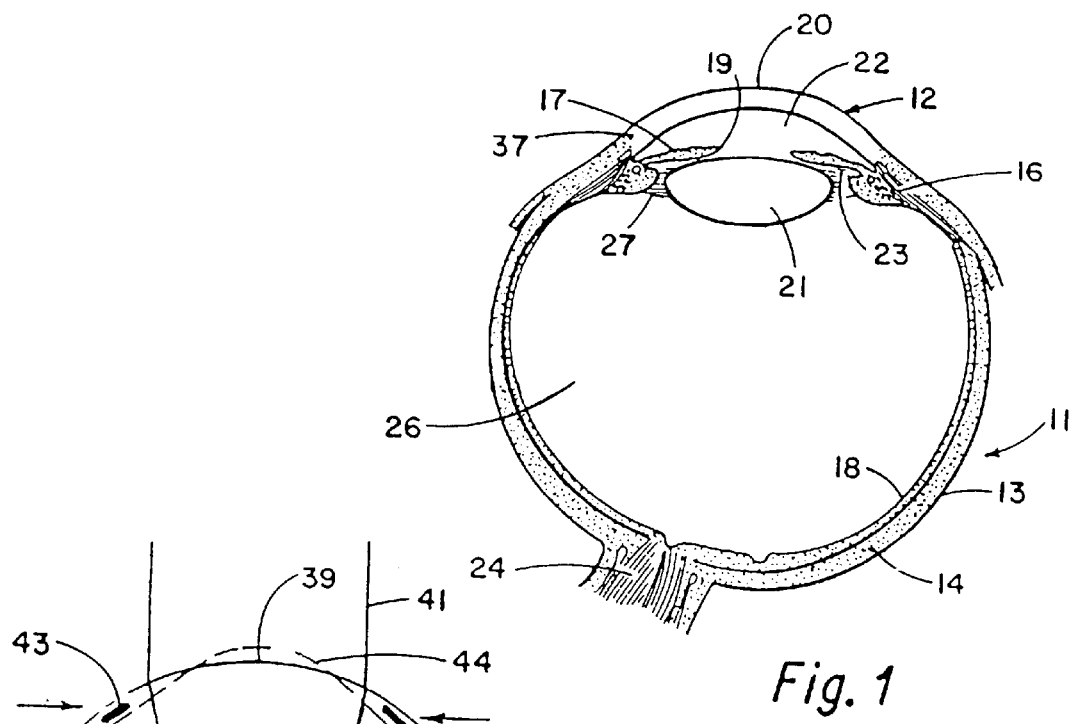
FIG. 1 is a schematic illustration of a horizontal section of the eye.

Referring first to FIG. 1 of the drawings, a horizontal section of the eye shows the globe of the eye resembling a sphere with an anterior bulged spherical portion 12 representing the cornea. Thus the eye is actually comprised of two somewhat modified spheres placed one in front of the other. The anterior of these two segments is the smaller more curved cornea.

The globe of the eye consists of three concentric coverings enclosing the various transparent media through which the light must pass before reaching the sensitive retina. The outermost covering is a fibrous protective portion the posterior five-sixths of which is white and opaque and called the sclera 13, and sometimes referred to as the white of the eye where visible to the front. The anterior one-sixth of this outer layer is the transparent cornea 12.

A middle covering is mainly vascular and nutritive in function and is comprised of the choroid 14, cibiary body 15 and iris 17. The choroid generally functions to maintain the retina. The ciliary muscle is involved in suspending the lens and accommodation of the lens. The iris is the most anterior portion of the middle covering of the eye and is arranged in a frontal plane. It is a thin circular disc corresponding to the diaphram of a camera, and is perforated near its center by a circular aperture called the pupil 19. The size of the pupil varies to regulate the amount of light which reaches the retina. It contracts also to accommodation, which serves to sharpen the focus by diminishing spherical aberration. The iris divides the space between the cornea 12 and the lens 21 into an anterior chamber 22 and posterior chamber 23. The innermost portion of covering is the retina 18, consisting of nerve elements which form the true receptive portion for visual impressions.

The retina is a part of the brain arising as an outgrowth from the fore-brain, with the optic nerve 24 serving as a fibre tract connecting the retina part of the brain with the fore-brain. A layer of rods and cones, lying just beneath a pigmented epitheluim on the anterior wall of the retina, serve as visual cells or photoreceptors which transform physical energy (light) into nerve impulses.

The viterous 26 is a transparent gelatinous mass which fills the posterior four-fifths of the globe. At its sides it supports the ciliary body 16 and the retina 18. A frontal saucer-shaped depression houses the lens 21.

The lens 21 of the eye is a transparent bi-convex body of crystalline appearance placed between the iris 17 and viterous 26. Its axial diameter varies markedly with accommodation. A ciliary zonule 27, consisting of transparent fibers passing between the ciliary body 16 and lens 21 serves to hold the lens in position and enable the ciliary muscle to act on it.

Referring again to the cornea 12, this outermost fibrous transparent coating resembles a watch glass. Its curvature is somewhat greater than the rest of the globe and is ideally spherical in nature. However, often it is more curved in one meridian than another giving rise to astigmatism. A central third of the cornea is called the optical zone with a slight flattening taking place outwardly thereof as the cornea thickens towards it periphery. Most of the refraction of the eye takes place on the surface of the cornea.

Figure 4:
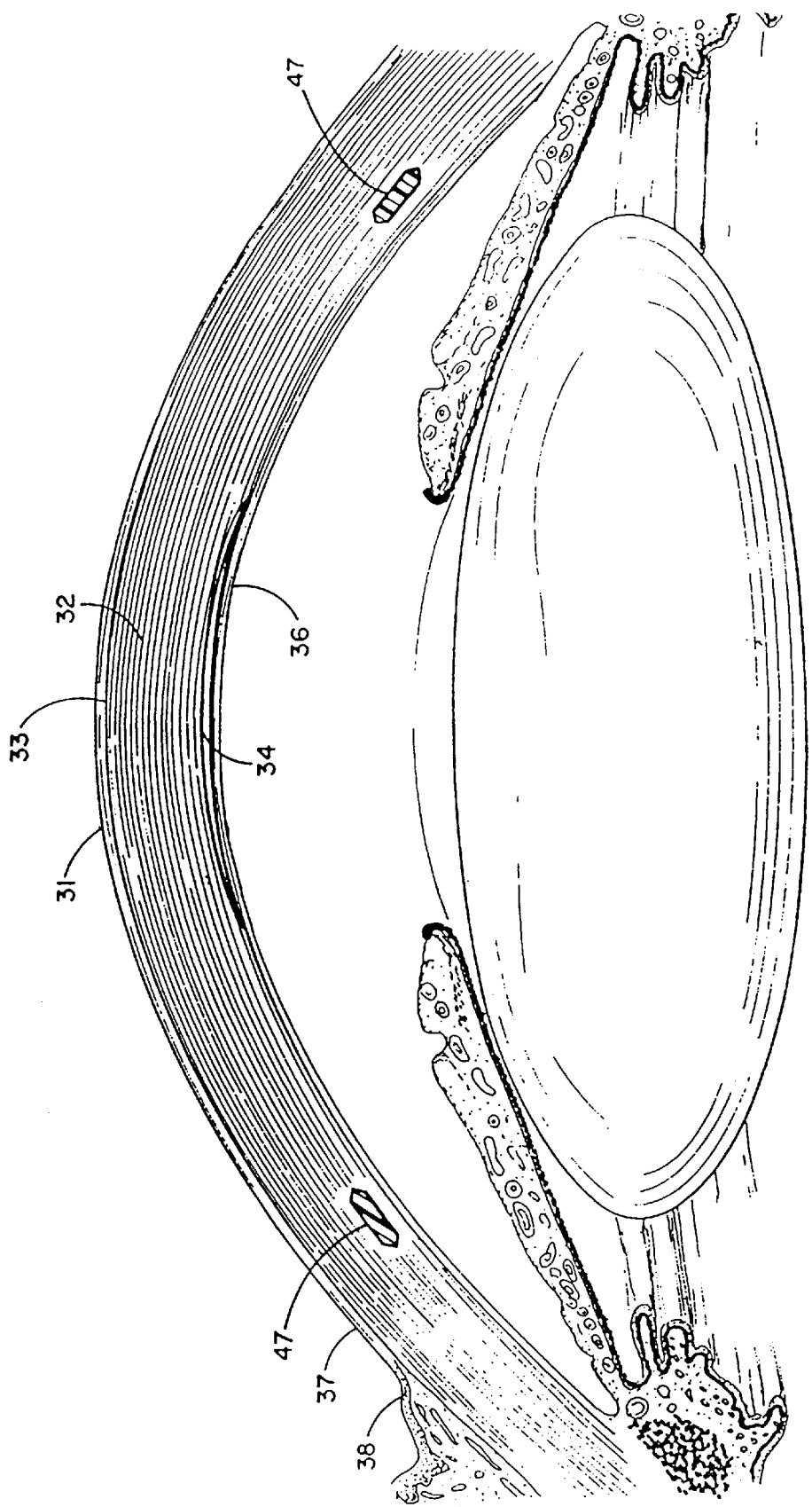
FIG. 4 is a detailed schematic illustration of a horizontal section of the frontal portion of the eye showing an adjustment ring of this invention positioned in the stroma of the cornea.
Figure 5:
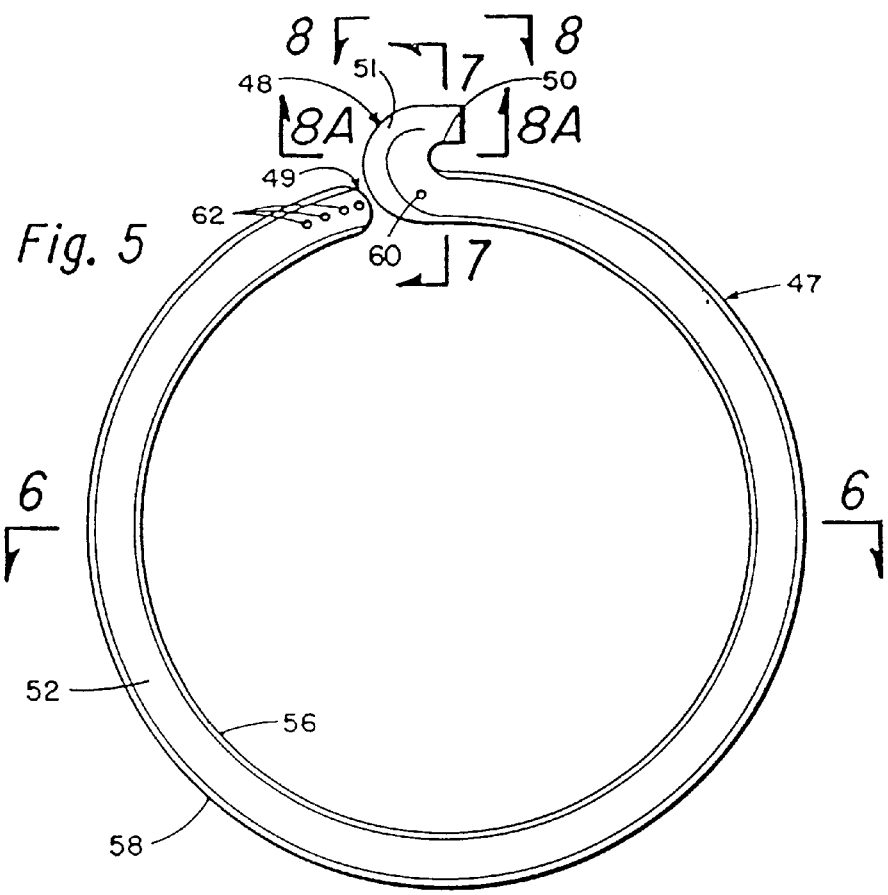
FIG. 5 is a plan view of a combination dissecting/adjustment ring showing its end portions.

Referring to FIG. 4, a more detailed drawing of the anterior portion of the globe shows the various layers of the cornea comprising an epitheluim 31. Epithelian cells on the surface thereof function to maintain transparency of the cornea. These epithelia cells are rich in glycogen, enzymes and acetylcholine and their activity regulates the corneal corpuscles and controls the transport of water and electrolytes through the lamellae of the stroma 32 of the cornea.

An anterior limiting lamina 33, referred to as Bowman's membrane, is positioned between the epithelium 31 and the substantia propria or stroma 32 of the cornea. The stroma is comprised of lamella having bands of fibrils parallel to each other crossing the hole of the cornea. While most of the fibrous bands are parallel to the surface, some are oblique, especially anteriorly. The fibrous bands within alternate lamella are at a near right angle to bands in the adjacent lamella. A posterior limiting lamina 34 is referred to as Descement's membrane. It is a strong membrane sharply defined from the stroma and resistant to pathological processes of the cornea.

The endotheluim 36 is the most posterior layer of the cornea and consists of a single layer of cells. The limbus 37 is the transition zone between the conjunctiva 38 and sclera 13 on the one hands and the cornea 12 on the other.

Figure 2:
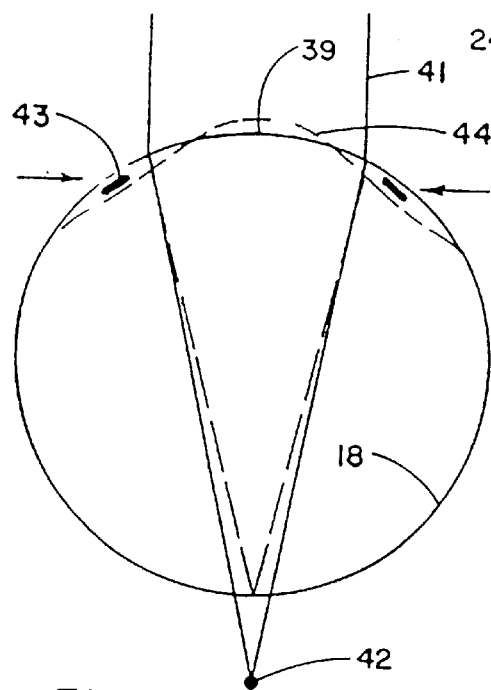
FIG. 2 is a schematic illustration of an eye system showing adjustment of the cornea to steepen the corneal slope.

Referring next to FIG. 2 of the drawings, the globe of an eye is shown having a cornea 12 with a typical patient's normal curvature represented by the solid line 39. If parallel rays of light 41 pass through the corneal surface 39 of FIG. 2 they are refracted by the corneal surfaces to converge eventually near the retina 18 of the eye. The diagram of FIG. 2 discounts, for the purposes of this discussion, the refractive effect of the lens or other portions of the eye. The eye depicted in FIG. 2 is hyperopic (far-sighted) and thus the rays of light 41 are refracted to converge at point 42 behind the retina. If a peripheral band of pressure is applied inwardly at the chord 43 of the cornea, the walls of the cornea are caused to steepen. This is because the volume of fluids within the anterior chamber 22 remains constant, thus the anterior portion of the cornea, including the optical zone (inner third of the cornea) steepens in slope to form a curvature (shown in exaggeration) following the dotted line 44. The rays of light 41 are then refracted from the steeper surface 44 at a greater angle to direct the refracted rays into focus at a shorter distance, such as directly on the retina 18.

Figure 3:
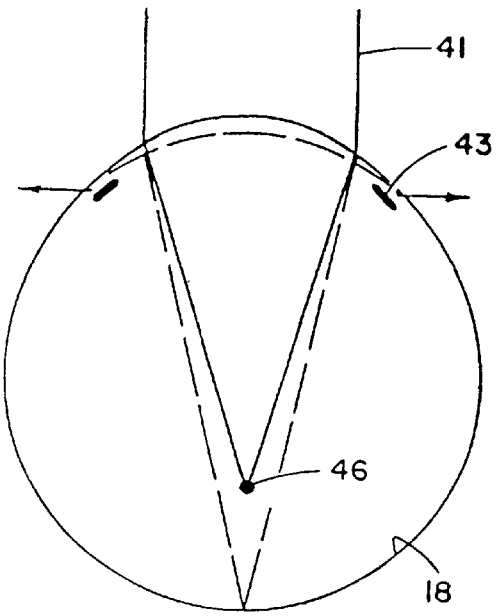
FIG. 3 is a schematic illustration of an eye system showing adjustment of the cornea to flatten the corneal slope.

FIG. 3 shows a similar eye system to that of FIG. 2 except that the so called normal corneal curvature of FIG. 3 causes the light rays 41 to refract into focus at a point 46 in the vitreous which is short of the retinal surface 18. This is typical of a myopic (nearsighted) eye. If chord 43 of the cornea is expanded uniformly outwardly as shown by the arrows, the walls of the cornea are flattened. Light rays 41 refracted by the now flattened corneal surface will be refracted at a smaller angle and thus converge at a more distant point such as directly on the retina 18.

The methods and apparatus of the present invention are concerned with a system for adjusting an annular chord of the cornea as suggested by the processes shown in FIGS. 2 and 3 to thereby correct refractive errors of the eye. Again referring to FIG. 4, a ring 47, having an ovaloid cross sectional shape is shown implanted in the stroma layer of the cornea. By adjusting the diameter of such a ring in the cornea and fixing that diameter at a discrete value, the rays refracted by the cornea and other eye components can be brought to focus directly on the retina 18. Such a ring placed typically at approximately the 8 mm chord of the cornea provides a means for making such a corrective adjustment. Apparatus and methods for making this adjustment are hereinafter described.

Figure 6:
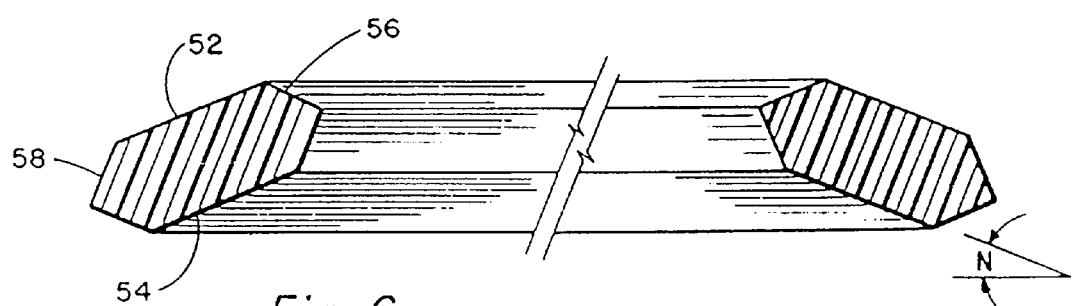
FIG. 6 is a sectional view taken along the line 6—6 of FIG. 5.
Figure 7:
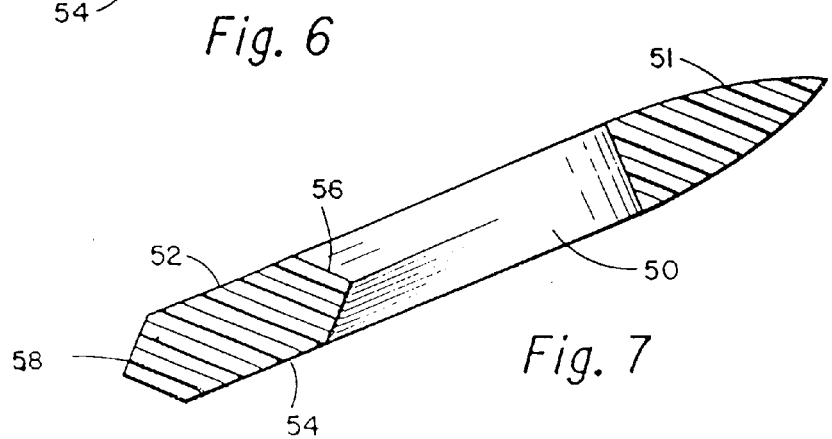
FIG. 7 is a sectional view taken along the line 7—7 of FIG. 5.
Figure 11:
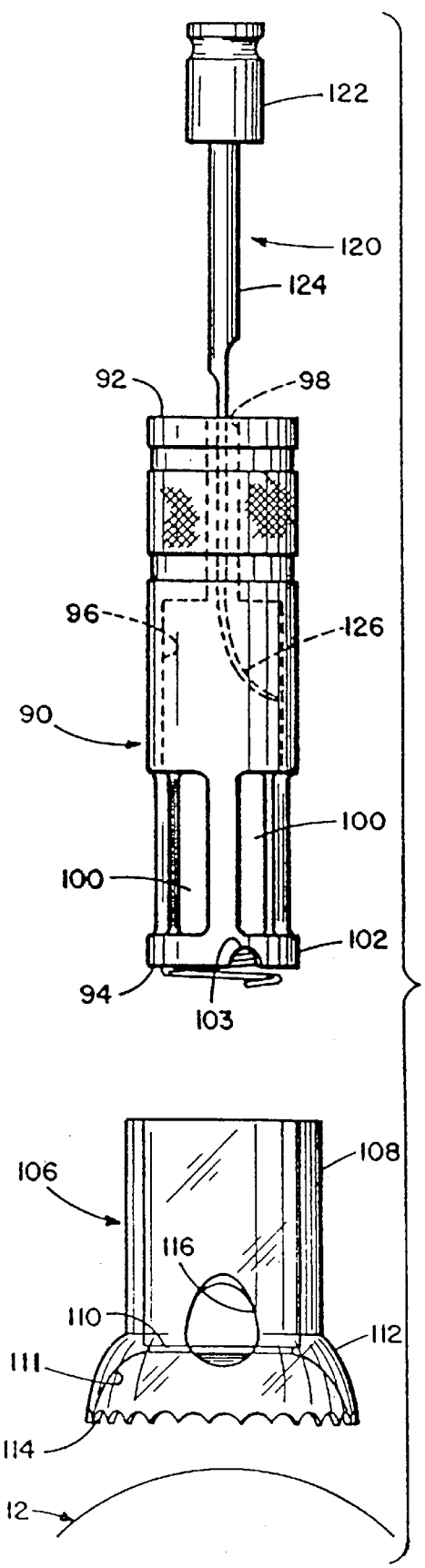
FIG. 11 is an exploded view of a ring holder apparatus used in this invention.

Referring now to FIGS. 5, 6, 7 and 8, the adjusting ring 47 is comprised of a generally circular member having split end portions 48 and 49. The ring is comprised of a material which has sufficient stiffness to maintain its generally circular shape and sufficient resiliency to permit ends 48 and 49 to be adjusted relative to one another to thereby enlarge or decrease the normal diameter of the ring at rest. The material should have properties that render it physiologically compatible with the tissue of the cornea. Two such materials are of plastic sold under the trademarks PLEXIGLASS and SAUFLON. Generally, materials made of hardened methyl Methacrylate or the like are acceptable. The forward end portion 48 of the adjusting ring 47 is enlarged to form a leading dissecting sharpened edge which, as it is driven through the stroma 32 of the cornea forms a tunnel for the trailing ring. The purpose of the enlarged edge as shown is to include a U-shaped opening 50 which is adapted to receive a drive ring as shown in FIGS. 9 and 10 for driving the ring into the cornea, provide clearance for the removal of the guide tool yet leave the plastic adjusting ring in situ within the cornea. The cross-sectional shape of the ring, as shown in FIGS. 6 and 7, comprises top surface 52 and a bottom surface 54 which are substantially parallel, and connected at their inner ends by a V-shaped rib 56 and at the outer end a V-shaped rib 58. In a preferred embodiment, the V-shaped ribs are formed by 45° intersecting surfaces, but could be at other intersecting angles. Of particular importance, is the forming of the adjusting ring such that the major axis of the ring is at an angle N which substantially corresponds to the slope of the corneal arc of the anterior pole of the cornea. Typically, this has been found to be an angle of 22½ degrees but varies from patient to patient. An opening 60 is provided adjacent to leading edge of adjustment ring 47 while a plurality of spaced openings 62 are found in the trailing edge. Once the adjusting ring has been in position, the required adjustment is retained by adhesives or by the insertion of a U-shaped clip 64 shown in FIG. 30.

Figure 12:
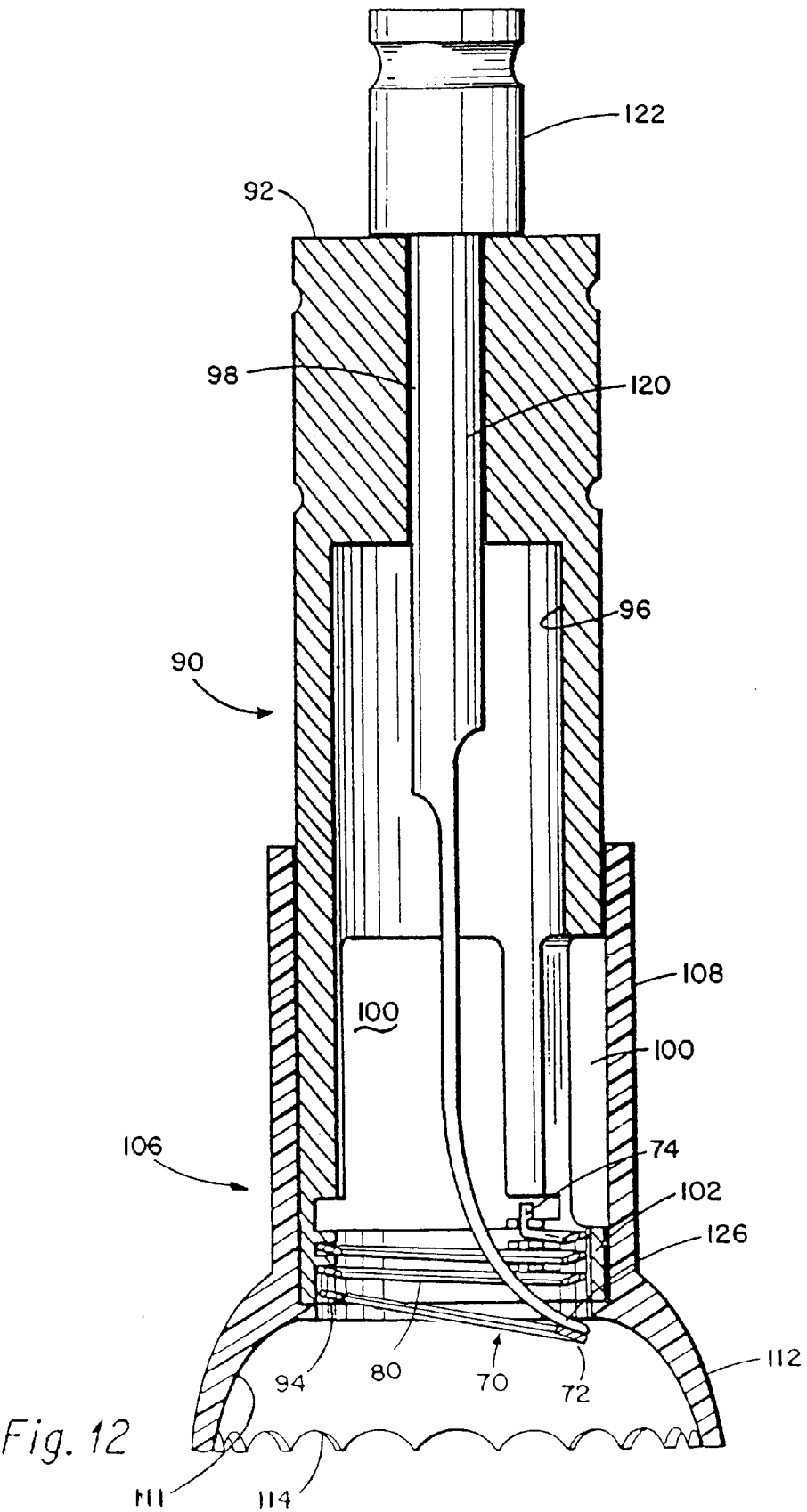
FIG. 12 is a sectional view of the assembled ring holder of FIG. 11.
Figure 18:
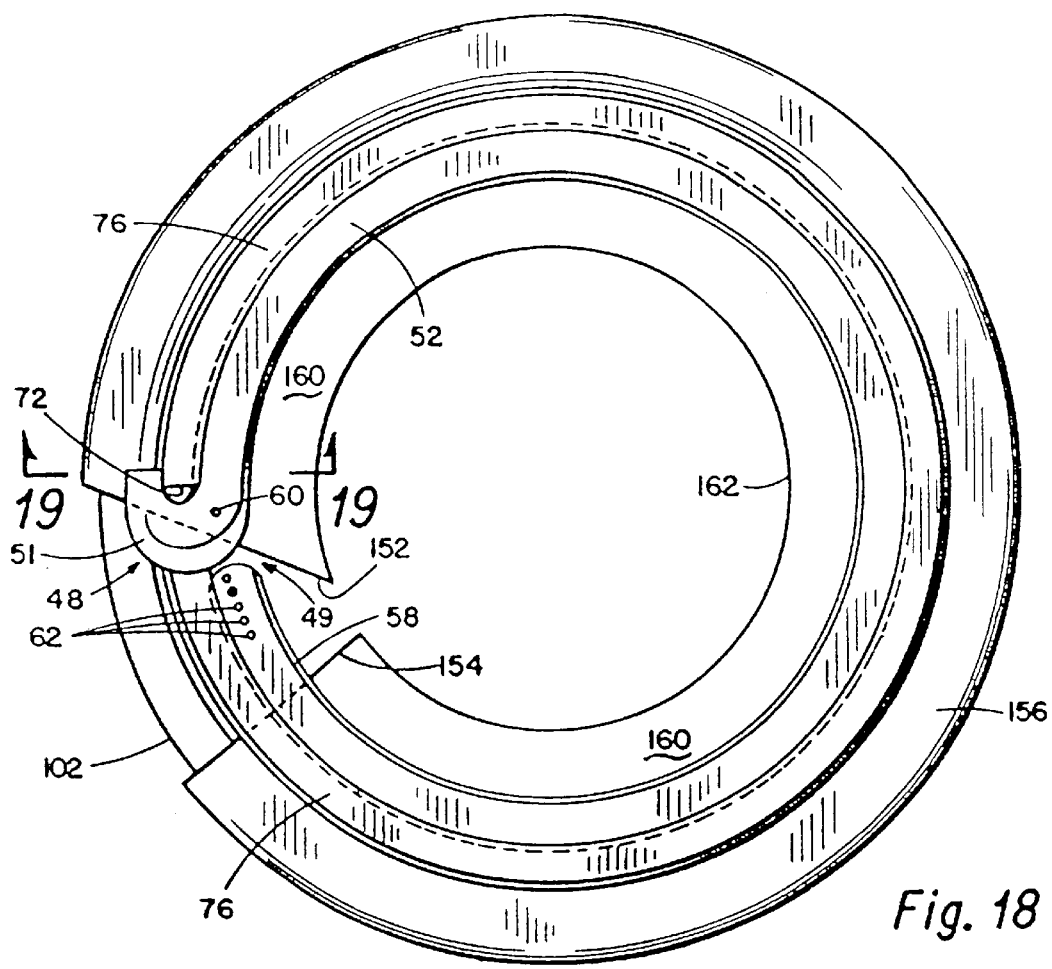
FIG. 18 is a bottom elevational view taken along the line 18—18 of FIG. 17.

Referring now to FIGS. 9 and 10, where is shown a drive ring 70 of the invention used to push and insert the adjusting ring 47 into its position. The ring is formed as a helical coil for use with the ring holder as hereinafter described. The drive ring has a leading edge 72 (see FIG. 12) terminating with an upright member 74 or other means for attachment and retention of the drive ring within a ring holder of this invention. As shown in FIG. 10, the ring is formed at a slope angle N substantially corresponding to the slope of said corneal arc as described for the adjustment ring. The cross-section of the ring is generally rectangular having a top side 76 and a bottom side 78 with an interior V-shaped groove 80 formed to match the V-shaped rib 56 of the adjusting ring. Preferably, the groove is formed by two 45° intersecting surfaces. One method of forming the edge coiled helical ring is schematically described in FIG. 29.

FIGS. 11, 12, 13 and 14 describe one form of ring holder of the invention which is adapted to retain and rotatably insert a curvature adjusting ring into the cornea of a patient's eye and is generally designated by the numeral 90. The holder is also adaptable to insert a dissecting ring followed by the insertion of an adjusting ring such as is described in related U.S. Pat. No. 4,452,235. However, the preferred use is to insert an adjustment ring such as described herein FIGS. 5–8 which ring includes a dissecting head. The holder is generally cylindrical having a top 92 and a bottom 94 and of diameter for use about a patient's eye. The bottom 94 includes means to releasably retain the adjustment ring and/or drive ring. The interior of the holder is substantially a hollow cylinder forming interior walls 96, shown by the dotted lines, which intersect thereabove with a smaller diameter opening 98, also shown dotted. A plurality of openings 100 are provided adjacent the lower end above a rim 102. The openings 100 are provided for the visual inspection by the surgeon during the operation. A guide cup, generally indicated by the numeral 106, is preferably made of a clear plastic material, again for the visual inspection by the surgeon, and comprises a cylindrical top portion 108 adapted to rotatably receive the bottom end of holder 90 which rests upon an interior shoulder 110. The cylindrical portion 108 is connected to a bottom semispherical skirt 112 having an inside curved surface 111 which may include a serrated bottom edge 114 or separately flexible fingers 115 (FIG. 11A) which surface 111, in its preferred use, is of a diameter so as to be positioned upon the limbus portion of the patient's eye permitting the cornea to be centered therein. An opening 116 is provided that extends both into the spherical skirt 112 and the cylindrical portion 108, again to provide visual acuity to the surgeon during the operation. A removable ring orientation blade, generally indicated by the numeral 120 includes a handle 122, a shaft 124 and a curved blade 126 shown dotted on the interior of the holder 90. The purpose of the blade can best be described with reference to the assembly view of FIG. 12 in that it is adapted to orient the tip of the dissecting blade and/or adjusting ring to enter the first incision in the corneal surface. The orientation blade 120 is thereafter removed and the rotation of the drive holder 90 causes the plastic ring to enter the stroma of the cornea and be guided properly thereby.

FIG. 12A describes an alternate embodiment of ring holder 300 and associated ring guide and orientation tool, generally designated by the numeral 302. The ring holder 300 is shown inserted into guide cup 106, previously described. FIGS. 12B and 12C depict the tool 302 specifically. The tool is made of plastic material, e.g. polyethylene which functions with a scissor-like movement caused by the shape. Two upper arms 304 and 306 are interconnected at a hinge 308 having opening 309 to two lower arms 310 and 312, the former of which has an outward tip 314. The upper arms 304 and 306 include respective stop pins 320 and 322. The function of the tool 302 is best shown in FIG. 12B. The inward movement of arms 304 and 306 causes a corresponding inward retracting movement of arms 310 and 312. In the retracted, dotted line, position the tool can be inserted into the tool holder 300. Releasing the arms causes the reverse outward movement permitting the tip 314 to be oriented relative to the direct ring 70 as shown in FIG. 12A, so that the drive ring 70 will be angularly oriented relative to the cornea. Stop pins 320 and 322 rest upon the top of holder 300, the location of which orients the ultimate position of tip 314. Upon rotation of the holder 300, the adjustmentsring will be caused to enter the stroma at the proper incision angle.

Figure 13:
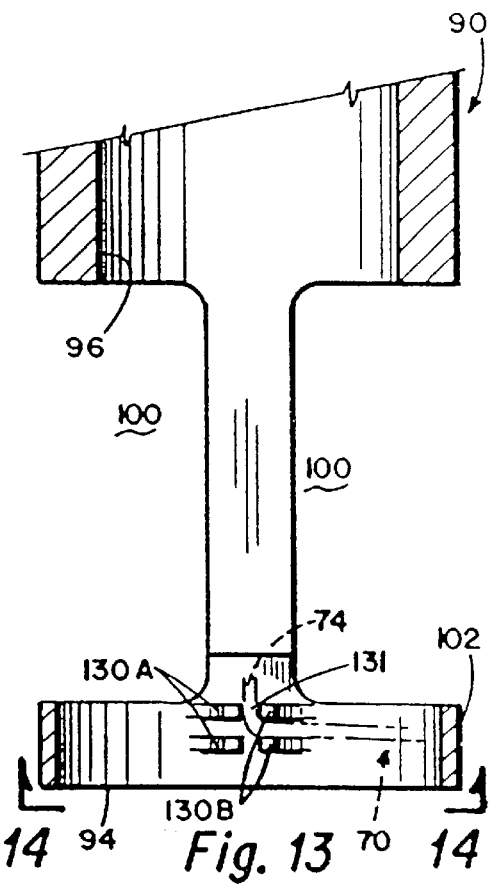
FIG. 13 is a partial sectional view of the bottom of the ring holder.
Figure 14:
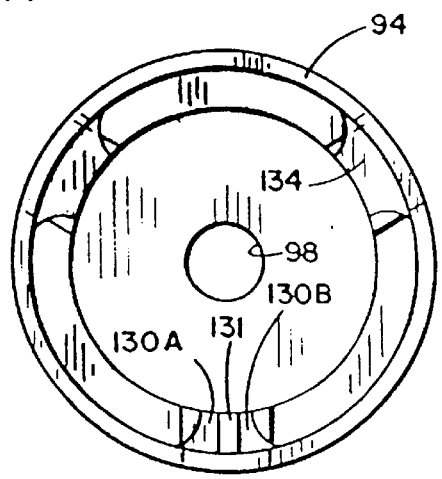
FIG. 14 is a bottom elevational view taken along the line 14—14 of FIG. 13.

As shown in the embodiment of FIGS. 13 and 14, the bottom rim 102 of the ring holder 90 includes a plurality of spaced ledges 130A and 130B which are provided to receive the coil of the dissecting and/or drive ring 70 with the insertion end to be ultimately oriented at the proper incision angle to the cornea. One of the ledges includes a spaced ledge 132 to receive the upright portion 74 of the drive ring 70 shown partially in phantom view. The means shown is not limiting as-other means to attach the drive ring may very well be suggested.

Referring now to FIGS. 15 through 19 an additional embodiment of the invention is disclosed as a utilizing guide cup 160 as a means to orient the drive/adjustment rings at the proper incision angle. The cup is positioned at the bottom of holder 90. The cup is circular in shape and split forming a leading edge 152 and a trailing edge 154. The cup is formed of a curved lip 156 around its outer periphery to fit over the bottom of rim 102 of holder 90 as shown in FIG. 17. The inner portion 160 is formed as a straight slope substantially corresponding to the slope N of the corneal arc of the anterior pole of the patient's cornea. At the center of the cup is an opening 162. The purpose of the guide cup can best be explained with reference to FIGS. 18 and 19 being to give support to ring 70 of FIG. 9 while hand assembling the adjustment ring 47 of FIGS. 5–7 into the vee groove 80 of drive ring 70 shown in FIGS. 9 and 10. Once assembled, the cup 150 is removed from the holder prior to surgery. The top elevational view of FIG. 18 describes the assembled combination.

Figure 19:
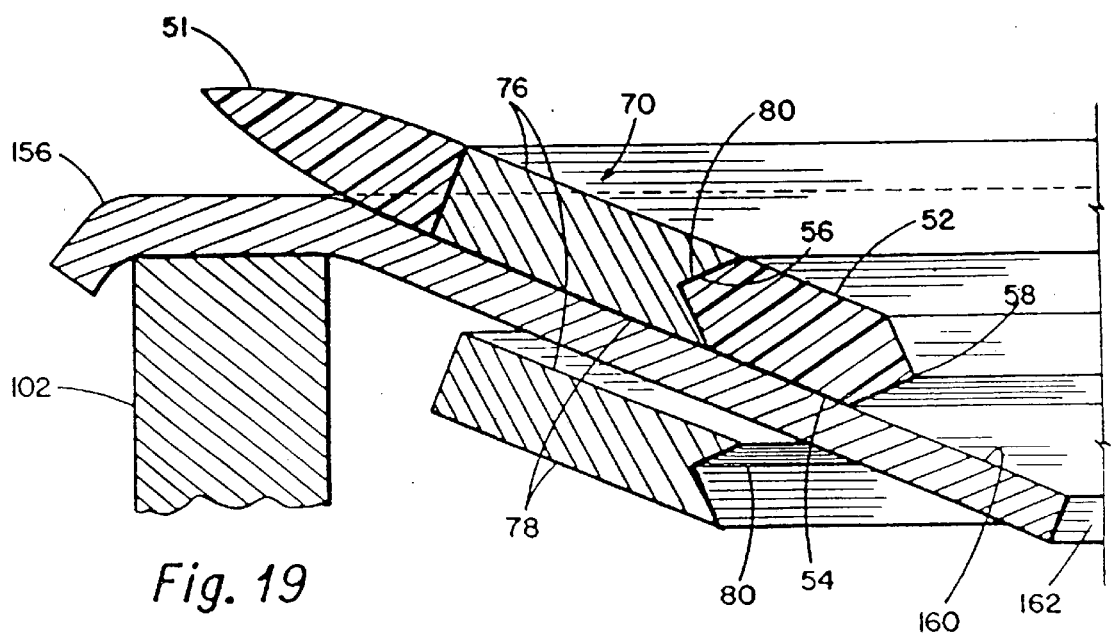
FIG. 19 is a sectional view taken along the line 19—19 of FIG. 18.

In the operation and use of this embodiment, the drive ring 70 would first be installed into the bottom rim 102 of holder 90. Thereafter, or previously thereto, the guide cup would be positioned at the bottom 94 of holder 90 threading the drive ring 70 such that it would be exposed upon surface 160 for at least one revolution. Thereafter, the corneal dissecting-adjusting ring 47 would be assembled to the drive ring such that rib 56 of the adjustment ring snuggly fits within groove 80 of the drive ring as shown in FIG. 19.

FIGS. 18A, 18B and 18C depict one embodiment wherein the trailing end 58 of adjustment ring 52 is radially compressed to a position under the forward portion of ring 52. A keeper sleeve 77, as shown, is positioned below the forward and initial entry portions of drive ring 76 and adjusting ring 52, which retains the adjustment ring and the drive ring 76 together until the surgical process of inserting the ring is complete. The keeper is a rectangular housing open at the forward end 79 and closed by a stop member 81 for half of the rearward end 83. The trailing end 58 abuts against the stop 81.

Prior to the actual insertion of the adjustment ring the cornea is marked using a tool 300, shown in FIGS. 31–34. The tool 300 is cylindrical with a series of points or serration 302 exposed at the bottom. Interiorly of the tool are a pair of intersecting cross-hairs 304 and 306 which permit the surgeon the align the tool relative to a given mark on the cornea. An incision marker 308 is at the bottom at an angle, e.g. 45° to the longitudinal axis of the tool 300. The marker 308 includes incision points 310 and 312 which extend downward. In use a non-toxic dye is used to cover the serrations 302 and point 310 and 312. The tool is then aligned and pressed against the cornea. The imprint of 310 and 312 provide a guide for the initial incision slit in the cornea which will become the place of entry for the adjustment ring 48. The actual entry is typically at about 80% of the depth from the anterior of the stroma.

Another embodiment of an adjustment ring interlock means is shown in FIG. 18D. The forward end includes a tapered opening 49 into which the rounded trailing end 47 is inserted once the adjustment ring 52 has been implanted within the cornea. The embodiment would necessarily apply where the adjustment ring size is already predetermined for a given eye correction. Thus assembled, holder 90 is then placed within guide 106 such that the bottom 94 rests upon rim 110 with the exposed dissecting/adjusting ring and drive ring positioned therebelow into the spherical skirt 112. This assembly is then positioned over the cornea of the eye at the place where the incision is to begin. The surgeon viewing through the translucent guide 106 and particularly through visual aid opening 116 is able to begin the incision by rotating holder 90. Upon such rotation, the dissecting head 51 prepares a path through the stroma of the cornea at the proper slope and rotated approximately one revolution. The holder is then reversed in direction permitting the drive ring to be rotated without the dissecting-adjusting ring being removed. Thereafter, through appropriate instrumentation and direction, the surgeon will adjust the ring by placing an appropriate U-shaped clip 64 into opening 60 and whatever opening 62 of the trailing edge 49 that will provide the correct corneal curvature adjustment.

Figure 30:
FIG. 30 is a side elevational view of a releasable clip used to connect the ends of an adjustment ring.

Referring now to FIGS. 20, 21 and 22, an alternate embodiment of the invention is disclosed for use with the holder 90 of this invention. In this embodiment, an edge coiled ring generally designated by the numeral 180 is coiled, as shown in FIG. 21 at a slope N. The forward end of the ring includes an enlarged sharpened end 182 forming the cutting surface for forming the pathway within the stroma of the cornea by the rotation of the holder 90 in the manner previously described. The rearward end of the coil includes an upright portion 184 for attachment within the spacing between ledges 130 and 132 (FIG. 13). Following the pathway formed by the dissecting ring and its remover the holder is then adapted to receive an adjustment ring as shown in FIGS. 23 and 24 or FIGS. 25 and 26 as described and incorporated herein by reference to U.S. Pat. No. 4,452,235. The adjusting ring is formed at a slope N and comprises an outer surface 186 and an inner surface 188. An opening 188 is provided at one end of the adjustment ring with a slot 190 and a plurality of openings 192 within a slot 194 to receive a clip 64 such as shown in FIG. 30 after the appropriate adjustment has been made.

Figure 25:
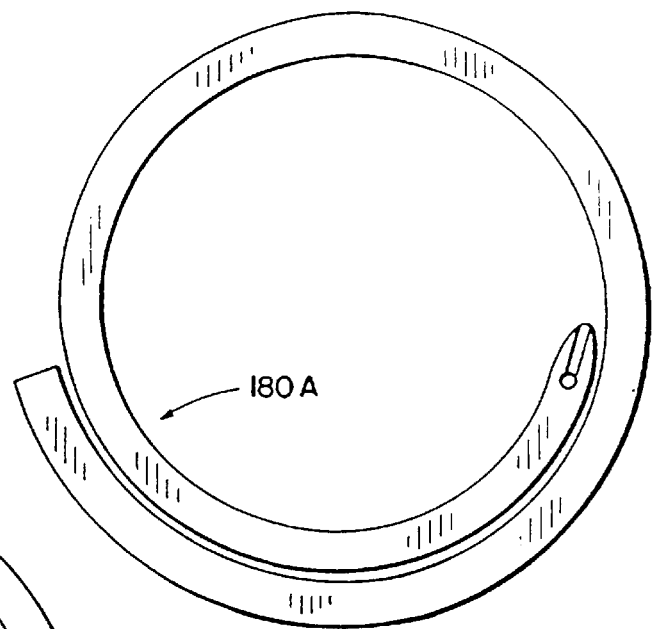
FIG. 25 and FIG. 26 are top elevational views of dissecting and adjustment rings as described in U.S. Pat. No. 4,452,235.
Figure 26:
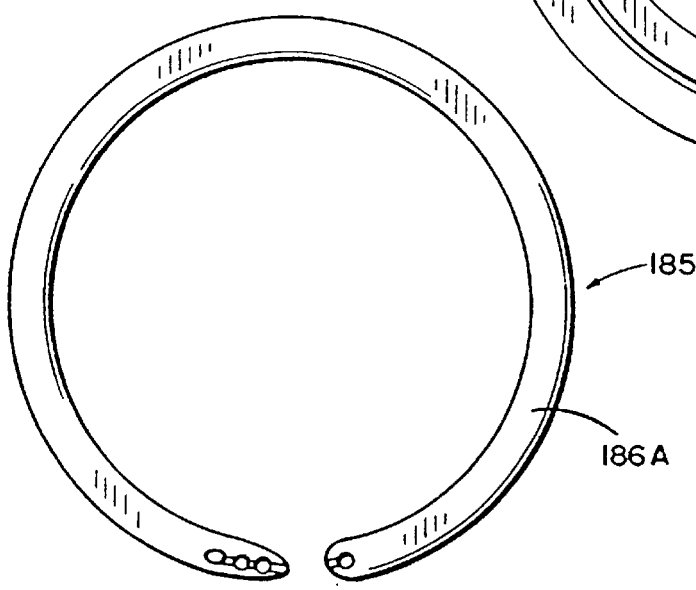
Figure 28:
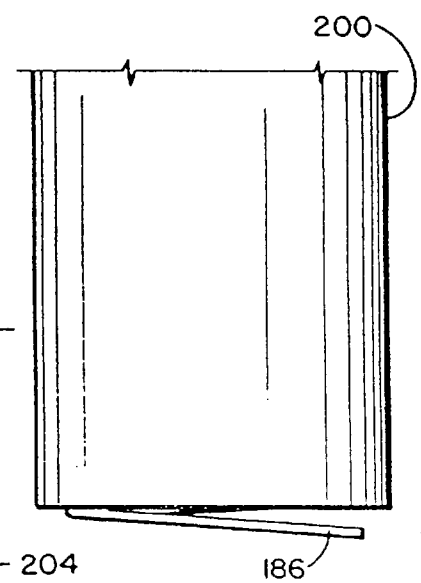
FIG. 28 is an elevational view of the ring holder of FIG. 27 including the assembled dissecting or adjustment ring.

FIG. 25 depicts a dissecting ring as described in the aforesaid U.S. Pat. No. 4,452,235 while FIG. 26 describes the adjusting ring which is also shown and described in the aforesaid patent.

Figure 27:
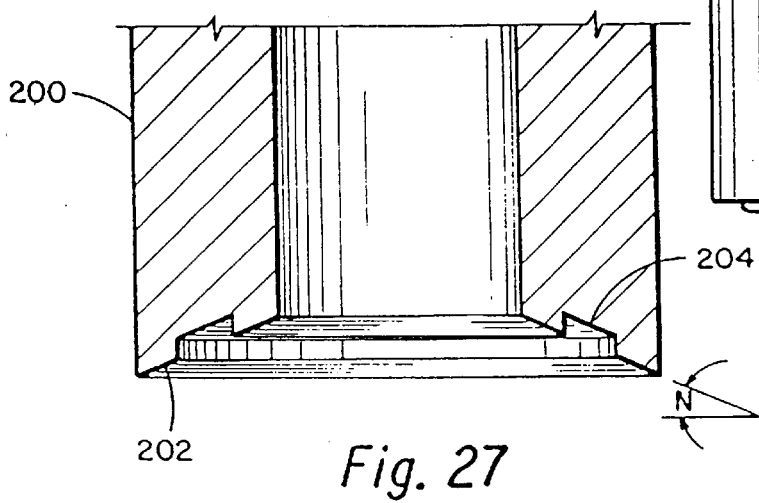
FIG. 27 is a bottom sectional view of another embodiment of a ring holder.

FIG. 27 is a cross-sectional view of an alternate embodiment of the invention of a holder 200 having at its end therein means to receive a dissecting and adjustment ring such as shown in FIGS. 20 through 26. The end of the holder is sloped at an angle N substantially equivalent to the corneal arc of the anterior pole of the cornea. Incorporated therein is a groove 204. The groove is of sufficient depth and width to support a dissecting and adjustment ring in radial compression yet release said ring at an appropriate time in the surgical operation.

Figure 29:
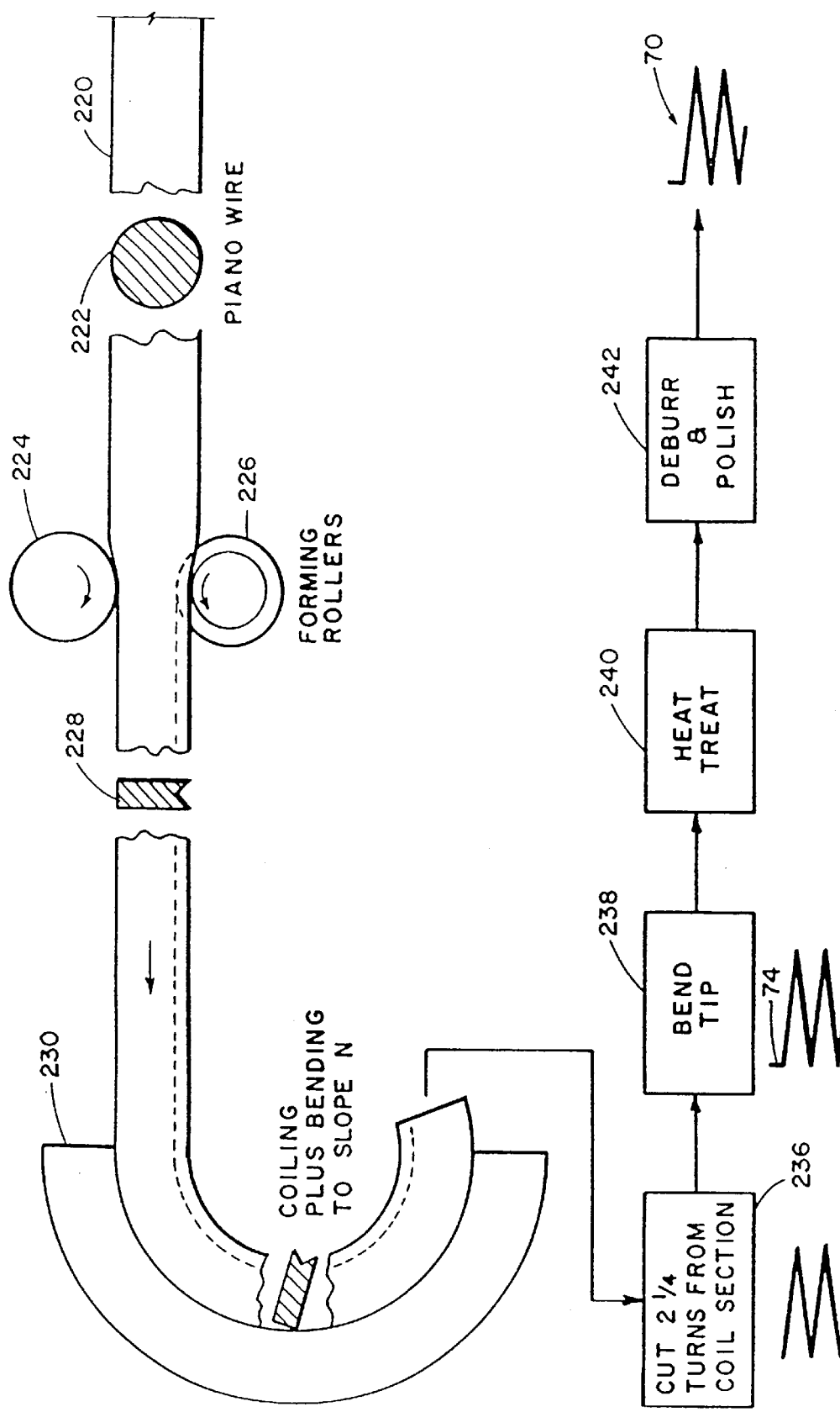
FIG. 29 is a schematic view describing one method for forming the sloped drive or dissecting ring of this invention.
Figure 31:
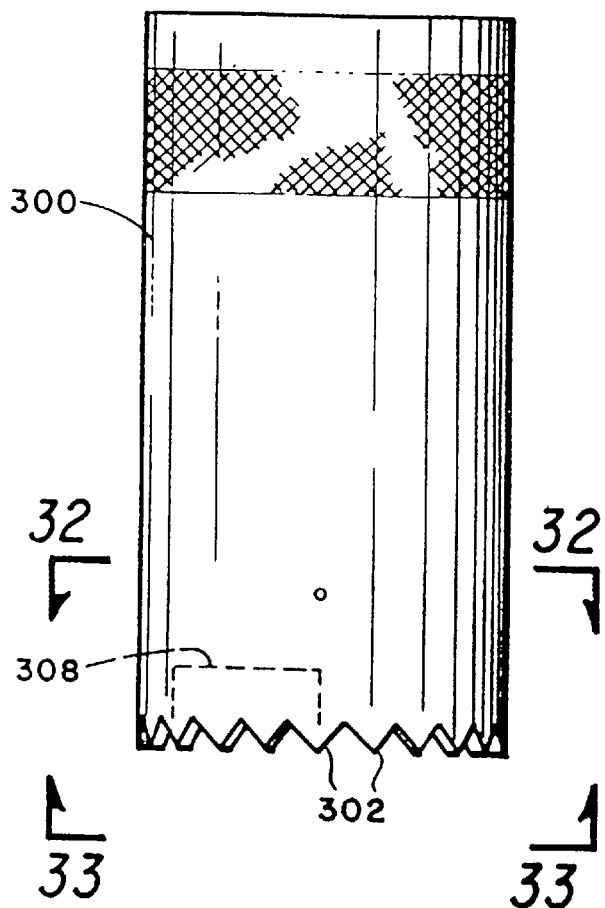
FIG. 31 is an elevational view of an instrument used to mark the cornea to identify the incision lines for the surgeon.
Figure 32:
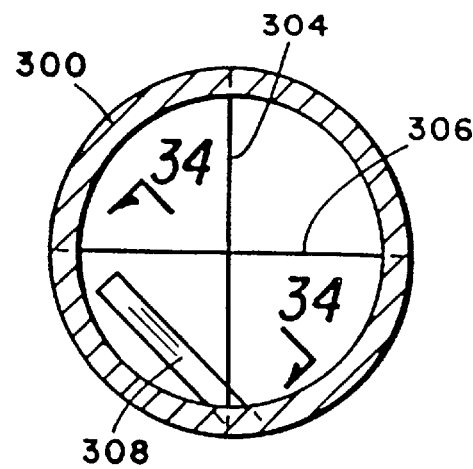
FIG. 32 is a top sectional view taken along the line 32—32 of FIG. 31.
Figure 33:
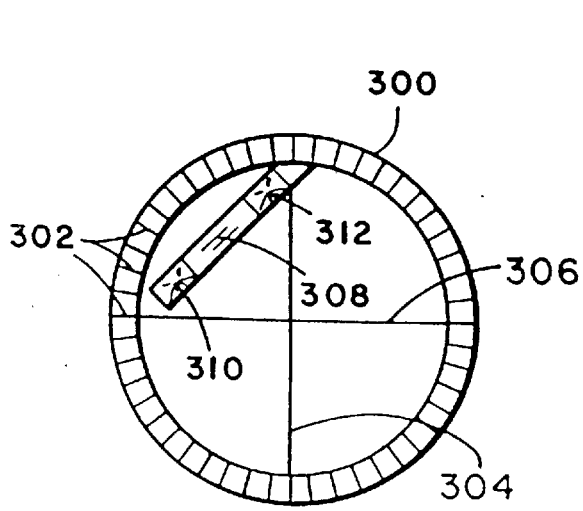
FIG. 33 is a bottom plan view taken along the line 33—33 of FIG. 31.
Figure 34:
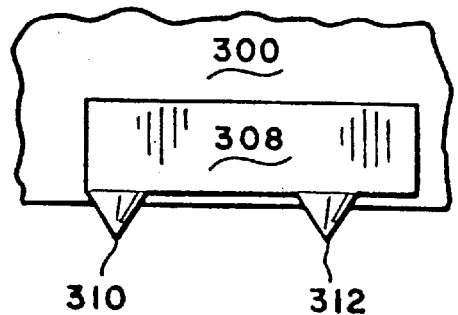
FIG. 34 is a partial section view taken along the line 34—34 of FIG. 32.

FIG. 29 is descriptive-schematic of a cold form process to form the edge coiled drive ring 70 or dissecting ring 182 of FIG. 20. In this process, the starting material is a steel wire 220 shown in circular cross-section at 222 which is forced through forming rollers 224 and 226 to form the rectangular cross-section 228. The forceful movement of the material is continued through a forming die 230 which edge coils the material and bends same to the desired slope N. Thereafter, as schematically shown, sections of the edge coiled material are cut as, for example, in 2¼ turns at station 236 followed by the formation of tip 74 at station 238. Thereafter the edge coiled material is heat treated at 240 followed by necessary deburring and polishing 242.

We claim:

1. Apparatus for marking a cornea of an eye comprising a hollow cylindrical member, a plurality of serrations in a circle at the bottom of said member; an incision marker at the bottom of said member, said marker having at least one incision point interiorily of said member and extending in a downwardly direction, and a pair of intersecting cross-hairs interiorily of said cylindrical member above said serrations.

2. An intracorneal implant comprising a split ring adapted for complete insertion into the cornea of a human eye for effecting refractive correction of said eye, said ring consisting essentially of a polymer and having a forward end and a rearward end, said forward end able to enter a pathway in said cornea for receiving said adjusting ring, and said adjusting ring having a non-ovaloid cross-sectional shape with opposing sides, wherein the sides define a top surface and a bottom surface of the ring.

3. The ring of claim 2 wherein the ring consists essentially of polymethyl methacrylate.

* * * * *